(12) United States Patent
Illathu Madhavamenon et al.

(10) Patent No.: US 11,179,432 B2
(45) Date of Patent: Nov. 23, 2021

(54) STABLE PALM INFLORESCENCE SAP POWDER COMPOSITIONS AND ITS PHARMACOLOGICAL EFFECTS

(71) Applicant: AKAY FLAVOURS & AROMATICS PVT LTD, Kerala (IN)

(72) Inventors: Krishnakumar Illathu Madhavamenon, Cochin (IN); Ratheesh Mohanan, Ochira (IN); Balu Paulose Maliakel, Kerala (IN)

(73) Assignee: AKAY FLAVOURS & AROMATICS PVT LTD, Kerala (IN)

( * ) Notice: Subject to any disclaimer, the term of this patent is extended or adjusted under 35 U.S.C. 154(b) by 140 days.

(21) Appl. No.: 16/068,769

(22) PCT Filed: Jan. 6, 2017

(86) PCT No.: PCT/IB2017/050056
§ 371 (c)(1),
(2) Date: Jul. 9, 2018

(87) PCT Pub. No.: WO2017/118944
PCT Pub. Date: Jul. 13, 2017

(65) Prior Publication Data
US 2019/0022164 A1    Jan. 24, 2019

(30) Foreign Application Priority Data
Jan. 7, 2016 (IN) .............................. 201641000570

(51) Int. Cl.
| | | |
|---|---|---|
| *A61K 36/889* | (2006.01) | |
| *A61K 36/00* | (2006.01) | |
| *A23L 2/52* | (2006.01) | |
| *A23L 33/16* | (2016.01) | |
| *A23L 33/15* | (2016.01) | |
| *A23L 33/105* | (2016.01) | |
| *A23L 2/39* | (2006.01) | |
| *A23L 3/46* | (2006.01) | |

(52) U.S. Cl.
CPC .............. *A61K 36/889* (2013.01); *A23L 2/39* (2013.01); *A23L 2/52* (2013.01); *A23L 3/46* (2013.01); *A23L 33/105* (2016.08); *A23L 33/15* (2016.08); *A23L 33/16* (2016.08); *A23V 2002/00* (2013.01)

(58) Field of Classification Search
None
See application file for complete search history.

(56) References Cited

PUBLICATIONS

JMMA Jayassundera et al. ("Spray-drying of coconut treacle into an amorphous powder" Emirates Journal of Food and Agriculture; 2014; vol. 26 (8); pp. 672-678) See IDS (Year: 2014).*
A. Rapeeporn et al. ("Effect of drying on total phenolic compounds, antioxidant activities and physical properties of palm sugar" Journal of Food Science and Agricultural Technology; 2015; vol. 1 (1); pp. 126-130). See IDS (Year: 2015).*
Aeimsard, R. et al., "Effect of drying on total phenolic compounds, antioxidant activities and physical properties of palm sugar," *Journal of Food Science and Agricultural Technology.*, 1 (1):126-130 (2015).
Akkarakaran, B.A., et al., "The health benefits of Neera; value addition potential," 2015. (http://www.coconutboard.in/images/media-fnbnews-3-8-15.pdf).
Borse, B.B. et al., "Chemical composition of volatiles from coconut sap (neera) and effect of processing," *Food Chemistry*, 101(3): 877-880 (2007).
Caparino, O.A., et al., "Effect of drying methods on the physical properties and microstructures of mango (*Philippine 'carabao'* var.) powder," *Journal of Food Engineering*, 111:135-148 (2012).
International Search Report for PCT/IB2017/050056. Filing date Jun. 1, 2017.
Jayasundera, J.M.M.A. et al., "Spray-drying of coconut treacle into an amorphous powder," *J. Food Agric.*, 26(8):672-678 (2014).
Yousefi, S. et al., "Effect of carrier type and spray drying on the physicochemical properties of powdered and reconstituted pomegranate juice (*Punica granatum* L.)," *J Food Sci Technol*, 48(6):677-684 (2011).

* cited by examiner

*Primary Examiner* — Michael Barker
*Assistant Examiner* — Randall O Winston
(74) *Attorney, Agent, or Firm* — Crowell & Moring LLP

(57) ABSTRACT

The present invention provides a coconut sap inflorescence powder compositions to provide symptomatic or prophylactic treatment of human disorder that has enriched vitamins, minerals, fat, carbohydrates and proteins. The invention also provides a process for producing such powders by spray drying or freeze drying. The powdered compositions and dosage forms are useful in the treatment of drug induced nephrotoxicity, alcoholic liver damage, and performance enhancement when administered orally.

4 Claims, 2 Drawing Sheets

STABLE PALM INFLORESCENCE SAP POWDER COMPOSITIONS AND ITS PHARMACOLOGICAL EFFECTS

CROSS REFERENCE TO RELATED APPLICATIONS

This application is a 371 national phase of PCT/IB2017/050056, filed Jan. 6, 2017, which claims the benefit of the filing date of Indian Application No. 201641000570, filed Jan. 7, 2016, the disclosures of which are incorporated, in their entirety, by this reference.

FIELD OF THE INVENTION

The present invention relates to the field of beverages and nutritional supplements and more particularly to nutritional compositions prepared from palm inflorescence sap. The present invention provides Neera in micronutrients enriched powder form, methods for their preparation and use. In particular, the present invention relates to methods for Spray drying and Freeze drying to produce stable Neera powder.

BACKGROUND OF THE INVENTION

The sweet sap obtained by tapping the unopened inflorescence of palm trees is identified as a nutritious natural drink rich in containing carbohydrates, minerals, vitamins, and amino acids with no alcohol content and low glycemic index. When collected from coconut trees, (Cocos nucifera), it is very often referred to as "Neera" in India, "Raa" in Sri Lanka, "Tuba" in Philippines, and "Tuvak" in Indonesia. Several food and beverage products including coconut sugar, jaggery etc, were developed from Neera by high temperature evaporation methods and available commercially. Several methods have been documented for the preparation and preservation of Neera in liquid form. However, the undesirable flavor and aroma characteristics of the liquid Neera make it uncomfortable while consuming. Moreover, rapid fermentation of Neera at ambient conditions also make it alcoholic drink, creating problems for storage and distribution.

Many methods have been standardised for the collection and preservation of inflorescence sap from various palm trees. The unopened spathe was selected for the extraction of sap. In a DFRL (Defends Food Research Laboratory, India) technology, sap was collected from the palm or coconut trees, chilled to 4° C. treated with clarifying agents, deodorisation was carried out with activated carbon or bentonite and filled in suitable bottles or containers with pasteurisation at 95° C. Since the extracted sap when allowed to ferment naturally or fermenting with yeast, juice can transform to "Toddy"—(a non-distilled alcoholic beverage of specific odour and taste).

DRDO (Defends Research and Development Organization, India) in collaboration with CFTRI (Central Food Technology Research Institute) developed the process for coconut sap (Neera) preservation without fermentation to alcohols (Toddy). The process include collection of sap from the unopened inflorescence of spadix and immediate chilling to 4° C., followed by filtration, chilling to 2 to 8° C., addition of acidulant citric acid (0.04 to 0.2%) and 10 to 15 ppm of nisin and pasteurization at 95° C. for 5 to 10 min for long term storage. Centrifugation at 4000 rpm for 10 min was also developed to remove the suspended particles. Heat processed Neera was found to be stable for 72 h. Though one year shelf-life was reported when processed by in-pack pasteurization or retort pouch processing, and storage under refrigerated conditions or 30 days under ambient conditions, it very often found to develop undesirable taste characteristics and odour making the consumption difficult.

Since the unfermented coconut sap (Neera) is photosensitive due to its ascorbic acid content, packaging based on PET/Aluminium foil was also developed for storage.

Yet another process provided a preparation of Neera by retaining all its cloudiness and natural constituents. Invention relates to a process for the preservation of deodourised Neera by removing the obnoxious odour. The process included the collection of sap, filtration, chilling to 2 to 8° C., and addition of bentonite or activated carbon black. Stirring the contents, centrifugation, and filtration followed by pasteurization or addition of preservatives provided Neera with natural cloudiness and minimized odour.

Many value added products have been developed from Neera i.e. Jaggery, palm syrup and palm sugar are the major products. Among the carbohydrates in Neera, sucrose is the main constituent with glucose, fructose, inositol, and raffinose as others. Glutamic acid, threonine and aspartic acid were identified as the major amino acids along with various vitamins. Neera has 84% moisture and 0.04% ether extractives (volatiles). The volatiles composed of ethyl lactate, phenyl ethyl alcohol, ethyl lactate, 3-hydroxy-2-pentanone, farnesol, 2-methyl tetrahydrofuran, and tetradecanone. However, the astringency and harsh note of the fermented Neera could be attributed to the increased amounts of acids (19.0 mg/1), such as palmitoleic acid and dodecanoic acid, along with higher concentrations of ethyl alcohol and ethyl esters (Food Chemistry, 2007, 101(3), 877-880).

Coconut syrup and sugar are commercially produced by boiling Neera and evaporating to dryness or honey like consistency with 60 to 70% brix. The process include boiling at high temperature for longer duration for evaporation which caused many of the volatile compounds to escape and vitamins to degrade, affecting the nutritional quality of original Neera. So majority of the attempts have been made to preserve into liquid form suitable for drinking as a beverage.

Current techniques provides a solution for preservation of Neera in liquid form under refrigeration for a limited period. Further the transportation, cold chain logistics, storage at reduced temperature, manufacturing with current technologies increase the cost of the product.

Thus there is a need exists to develop simple, cost-effective methods for preparation and long term storage of Neera without affecting the nutritional characteristics. The enrichment of the nutritional factors in neera will also be interesting for the development of Neera having significant pharmacological activities. Also, lies requirements for the development of suitable forms of Neera without any undesirable taste or aroma characteristics. Thus, the present invention provides the Neera in powder form that is stable at room temperature and containing enriched levels of nutritional factors than in liquid Neera, sufficient enough to trigger pharmacological activities when consumed orally. Neera in powder form is easy to transport, store and can be easily reconstituted with water to make natural health drink instantly.

SUMMARY OF THE INVENTION

In an embodiment, the present invention relates to dry neera powder suitable for oral administration comprising proteins, fat, carbohydrates, vitamins and minerals. In an embodiment, the present invention relates to process for the preparation of stable neera powder from fresh coconut sap inflorescence by spray drying or freeze drying process.

In an embodiment, the present invention also provides method of treating drug induced nephrotoxicity in a mammal which method comprises administering to said mammal a therapeutically effective oral dosage form comprising powder Neera. In an embodiment, the present invention also provides method of ameliorating alcoholic liver damage in a human subject which method comprises administering to said subject a therapeutically effective oral dosage form comprising powder Neera.

In an embodiment, the present invention also provides method for extending endurance during exercise and improve the muscle performance in a subject by administering the Neera powder.

DETAILED DESCRIPTION OF THE INVENTION

Figure 1:
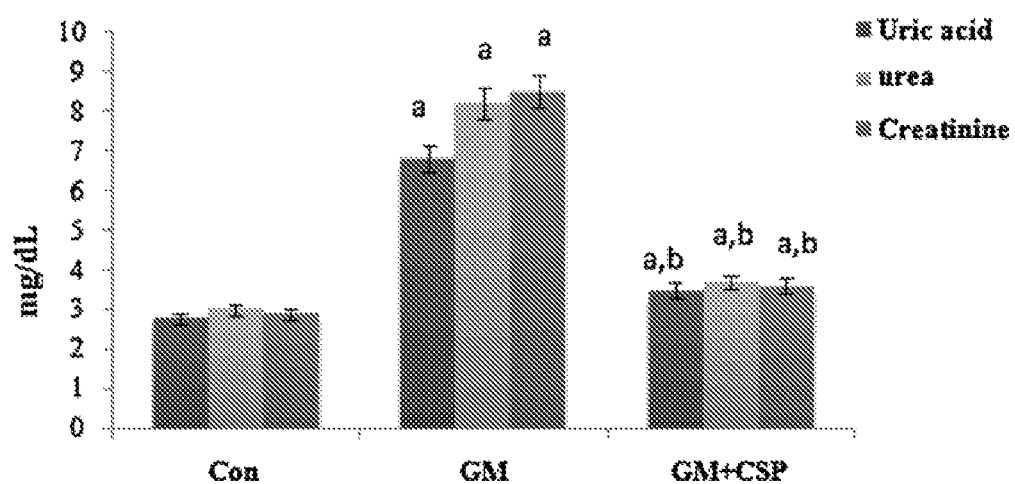
FIG. 1 shows Effect of CSP on the Kidney function

The term "Neera" as used herein refers to unfermented inflorescence sap collected from any of the palm trees, capable of producing the same.

The term "Fresh Neera" refers to the inflorescence sap collected from the palm trees, immediately after collection, stored under controlled temperature to avoid fermentation.

The terms "palm inflorescence sap", "coconut inflorescence sap", "coconut sap juice", "palm sap juice", "Neera" constitutes same meaning, are being used interchangeably throughout the document.

The terms "Neera powder", "coconut inflorescence sap powder", "coconut sap powder", "CSP" are being used interchangeably throughout the document to refer powder form prepared from liquid coconut sap inflorescence.

In an embodiment, the present invention relates to dry neera powder suitable for oral administration comprising proteins, fat, carbohydrates, vitamins and minerals.

In an embodiment, the present invention relates to preparation of neera in powder form suitable for oral administration comprising proteins, fat, carbohydrates, vitamins and minerals.

In an embodiment, the vitamins include vitamin C, vitamin B1, vitamin B2, vitamin B3, vitamin B6, vitamin B7 and vitamin B9 in the range of 500-1500 ppm, 1000-5000 ppm, 200-800 ppm, 100-1000 pm, 500-1500 ppm, 5-15 ppm and 5-15 ppm respectively.

In an embodiment, the minerals include potassium, sodium, magnesium, phosphorus, zinc, iron, copper and manganese in the range of 4000-8500 ppm, 150-250 ppm, 145-242 ppm, 4-10 ppm, 1-3 ppm, 0.5-5 ppm respectively.

In an embodiment, the carbohydrate is in the range of 60 to 80%.

In an embodiment, the fat is in the range of 0.5-1.5%.
In an embodiment, the protein is in the range of 0.5 to 2%.

The present invention relates to neera obtained in powder form from fresh coconut sap inflorescence, with the same or enhanced nutrient profile of the value of fresh coconut inflorescence sap.

In an embodiment, the present invention relates to dry neera powder capable of reconstitution with water, maintaining the same or enriched nutritional value of fresh coconut inflorescence sap.

The present invention relates to process for the preparation of stable neera powder from fresh coconut sap inflorescence. The process is particularly suitable for liquids that cannot be stored for longer period.

In an embodiment, the invention relates to process for the preparation of stable neera powder from fresh coconut sap inflorescence by spray drying or freeze drying process.

In an embodiment, the neera powder according to the present invention maintains the same or enhanced nutrient profile of the original liquid when reconstituted to liquid.

In an embodiment, the present invention provides a process for the preparation of stable inflorescence sap powder comprising the steps of a) The fresh neera obtained from the palm inflorescence sap, is filtered to provide the liquid starting material
b) Mixing the filtrate with carrier or encapsulating agent to form homogenized emulsion
c) Homogenizing the said mixture in a pressure range and speed
d) Spray drying the homogenate to form a dried powder composition of Neera powder with all the nutrient values of the fresh Neera In an embodiment, the fresh neera obtained from the palm trees by tapping or by using the well-known traditional techniques known in the art. The fresh neera which is tapped in 2 to 3 hr is cooled to less than 4° C. to avoid fermentation. Alternatively the fermentation can also be prevented using other known techniques, using anti fermenting solutions and specialized containers.

The unfermented neera is filtered to remove any fine particles in the fresh Neera. In and embodiment, the filtration is performed using 300 mesh filter cloth that essentially removes all the impurities i.e. particulate matter.

In an embodiment, the neera filtrate is mixed with carrier or encapsulating agent to make the liquid suitable for spray dying. The carrier provides the structure of the dried product without interacting directly with the biologically active compounds.

In an embodiment, the carrier and/or encapsulating agent is selected from the group consisting of gum acacia, gum arabic, gum gatti, xanthum gum, maltodextrin, starch, modified starches, sugars, natural polysaccharides, dietary fibers, proteins, other food grade neutral materials such as cereal flours, botanical extracts, polyvinyl alcohol, polyethylene glycols and mixtures thereof.

The combination of Neera and carrier will form a homogenized mixture to form an emulsion. The combination of the carrier and neera may form a solution, emulsion or suspension. Homogenizers can be used to get effective encapsulation and also in reduce the particle size to nano ranges. The homogenization is achieved by using rotor-stator homogenizers or high pressure homogenizers or ultrasound aided homogenizers.

The selection of homogenizer varies widely based on the carrier material. Suitable homogenizer is selected that can form uniform emulsion. In certain embodiments more than one homogenizer technique is employed to form homogeneous emulsion.

In an embodiment, the homogenization by high pressure homogenizers is performed in the pressure range of 10-150 Mpa, most preferably at 20 to 40 Mpa.

In an embodiment, the homogenization by rotor-stator homogenizers is about 10000-30000 rpm, most preferably about 15000-20000 rpm.

In an embodiment, the homogenized mixture is subjected to spray drying to obtain a stable neera powder. Spray drying is the process of converting the mixture in its liquid form to a powder by dehydrating or drying a fluid containing one or more compounds. The process removes the moisture component from the liquid solution. The solution is sprayed through a nozzle into a chamber that simultaneously has hot air being blown into it. As droplets of the solution are released through the nozzle and come in contact with the hot air, the moisture content of each droplet is removed, thus turning it from liquid to powder.

In an embodiment, the condition for spray drying includes an "inlet temperature" which is the temperature at which the solution enters the spray dryer, an "outlet temperature" is the temperature at which the gas exits the spray dryer.

In an embodiment, the gas inlet temperature during spray drying is about 50° C. to about 160° C., preferably 120° C. to about 160° C. Most preferably, the gas inlet temperature is about 140° C. to about 160° C., where the liquid flow rate at 40-50 Lit/h. Inlet and outlet temperature may vary depending on the flow rate of the feed material and capacity of the spray driers.

In an embodiment, the outlet temperature is preferably below the inlet temperature, the outlet temperature is about 50° C. to about 100° C., preferably 80° C. to about 100° C. Most preferably, the outlet temperature is about 85° C. to about 95° C.

In some embodiments, the inlet or outlet temperatures may be varied, if necessary, depending on the equipment, gas, or other experimental parameters. For example by employing the specialty spray dryers, drying can be achieved at low temperature of 40-80° C. However maintaining the nutritional value of the end product is critical for the efficacy of the product.

In an embodiment, the invention relates to a process for the preparation of stable neera powder from a liquid coconut inflorescence sap and accompanying substances by freeze drying, comprising the steps of a) Obtaining a liquid coconut inflorescence sap starting material from unopened inflorescence of palm trees;

b) Subjecting the liquid starting material of step (i) to one filtration step to obtain a purified liquid starting material;

c) Mixing the purified liquid starting material of step (ii) with carrier or encapsulating agent;

d) homogenizing said emulsion in step (iii) in a pressure range and speed to form a homogenate;

e) the mixture obtained in step (iv) is frozen at −40 to −80° C., preferably at −45 to −60° C.;

f) the frozen material in step (v) is subjected to primary drying in vacuum at −45 to −60° C.;

g) the primary dried material in step (vi) is subjected to secondary drying;

h) recovering the stable neera powder after secondary drying.

In an embodiment, the filtration is performed using less than 300 mesh.

In an embodiment, the carrier or encapsulating agent is selected from the group consisting of gum acacia, gum Arabic, gum gatti, xanthum gum, maltodextrin, starch, modified starches, sugars, natural polysaccharides, dietary fibers, proteins, other food grade neutral materials such as cereal flours, botanical extracts, polyvinyl alcohol, polyethylene glycols and mixtures thereof.

The palm inflorescence sap is mixed with suitable carrier to make the liquid suitable for freeze drying. The mixture is homogenized using a homogenizer to make a uniform emulsion.

In an embodiment, the homogenization is performed in the pressure range of 10-150 Mpa, most preferably at 20 to 40 Mpa.

The said process of freeze-drying an aqueous palm inflorescence sap comprises the distribution of the liquid product in containers closely fitted in cavities of a tray-shaped heat-conducting solid material block having relatively high heat transfer, and further subjecting the block to accelerated cooling. The frozen mixture is dried under vacuum in the block so that the frozen product in each container is dried at substantially the same rate.

The homogenized emulsion is loaded into freeze drying containers and frozen in the temperature of about −40° C. to −80° C., preferably about −45° C. to −60° C. The frozen material is subjected to drying under vacuum at a temperature range of −45° C. to −60° C. to form powder. Further the primary powder is secondary dried to further remove moisture content to form a free flowing powder Neera.

In an embodiment, wherein the temperature during freezing is about −40° C. to about −80° C., most preferably about −45° C. to about −60° C.

In an embodiment, the frozen material is subjected to primary drying under vacuum at a temperature of about −45° C. to about −60° C.

In an embodiment, the primary dried material may be subjected to secondary drying to further remove the moisture content.

In another embodiment, the palm inflorescence sap powder may also prepared using other techniques that are well known in the art. Refractance Window Drying, drum drying etc which are used for the conversion of solution into powder can also be used for the preparation of sap powder. Refractance Window Drying is the gentlest method to dry fresh foods. It is a unique, self-limiting dehydration method that uses infra-red light, rather than direct extremes of temperature, to remove water from food. Relying on the conductivity of water together with the properties of infrared and the refractance of light, it is recommended for preserving the precious nutrients and phytonutrients found in foods.

The Neera powder obtained by any of the above processes is white, free flowing, instantly water soluble, non-hygroscopic, and stable when stored at room temperature. It has been found the Neera powder when stored at room temperature (below 30° C.) has a shelf life of more than 24 months. The Neera in the powder form is stable even at room temperature, thus avoiding special storage requirements.

In an embodiment, the neera powder according to the present invention has a moisture content about less than 6 percent.

In an embodiment, the neera powder is substantially amorphous.

The powder when reconstituted with water, completely soluble, forms a transparent solution with no sedimentation. Both the powder and solution is devoid of unpleasant smell and taste characteristics yet providing all the nutritional benefits naturally.

The Neera powder obtained by the present invention is stable and doesn't include any synthetic excipients/carriers/preservatives thus making the product completely natural.

The powder retains all the nutritional benefits of Neera, thus consists carbohydrates, proteins, fat, minerals, vitamins, amino acids and polyphenols. It is observed that the nutrient levels are 3-5 times higher compared to liquid form.

The glycemic index of the Neera powder is low compared to processed sugars, thus offers a suitable alternative natural solution for sports and energy drinks, also for diabetic population.

In another embodiment, the powder is suitable for the preparation of various dosage forms including, but not limited to tablets, granules, pellets, capsules, syrups, soft gels, sachets, carbonated beverages, dispersible tablets, carbonated tablets, ready-to-drink powders etc.

In an embodiment, the powder is suitable to blend with other vitamins, minerals, proteins, carbohydrates, fats and other bioactive phytochemicals or fruit/vegetable powders or extracts to produce unique food or functional food or medical food.

The term "therapeutically effective amount" is the amount present in the composition that is needed to provide the desired level of Neera powder in the subject to be treated to give the anticipated physiological response. This amount is desired for each indication on a case-by-case basis. The term "physiologically effective amount" is that amount delivered to a subject to give the desired palliative or curative effect.

The therapeutically effective amount of powder Neera will vary in composition depending on the biological activity of the Neera powder employed and the amount needed in a unit dosage form.

In an embodiment, the present invention provides method of treating drug induced nephrotoxicity in a mammal which method comprises administering to said mammal a therapeutically effective amount of powder Neera.

Nephrotoxicity induced by gentamicin is clinically known as a nonoliguric renal failure with characterized change in serum creatinine levels and a hypo-osmolar urinary output. Gentamicin also causes cell death by generation of free radicals, phospholipidosis, extracellular calcium-sensing receptor stimulation and energetic catastrophe, reduced renal blood flow and inflammation.

In certain embodiments, the method treats drug induced toxicity through amelioration of at least one anti-oxidant enzymes selected from the group comprising of SOD (superoxide dismutase), CAT (catalase), GSH (Glutathione) and GPx (glutathione peroxidase); amelioration of at least one anti-inflammatory maker selected from the group comprising of Interleukin-6 (IL-6), Tumor Necrosis Factor-α (TNF-α), TLR-4, iNOS; reducing at least on one elevated renal enzymes selected from the group comprising of Creatinine, uric acid and urea.

In an embodiment, the present invention also provides method of ameliorating alcoholic liver damage in a mammal which method comprises administering to said subject a therapeutically effective amount of powder Neera.

In an embodiment, the method ameliorates alcoholic liver damage through a) amelioration of at least one biomolecular marker selected from the group comprising of SGOT, SGPT, Alkaline Phosphatase (ALP), C-Reactive Protein (CRP), COX, Interleukin-6 (IL-6), Tumor Necrosis Factor-α (TNF-α), TLR-4, Matrix metalloproteinase (MMP)-2, Matrix metalloproteinase (MMP)-9; amelioration of at least one anti-oxidant enzyme selected from the group comprising of SOD (superoxide dismutase), CAT (catalase), GSH (Glutathione) and GPx (glutathione peroxidase).

In an embodiment, the present invention provides method of extending endurance during exercise and improve the muscle performance in a subject by administering an effective amount of Neera powder. The neera powder rich in minerals and vitamins also aids for immediate replenishment of the same.

In an embodiment, the method extends endurance during exercise through amelioration of at least one anti-oxidant enzymes selected from the group comprising of SOD (superoxide dismutase), CAT (catalase), GSH (Glutathione) and GPx (glutathione peroxidase); amelioration of at least one anti-inflammatory maker selected from the group comprising of Interleukin-6 (IL-6), C-Reactive Protein (CRP); reducing muscle injury during exercise or physical activity by reducing or maintaining the serum creatine kinase (CK) and lactate levels.

Various embodiments are directed to a method for treating a subject, by administering therapeutic effective amount of neera powder composition 250 mg to 10 g/day, offers wide health benefits, including but not limited to athletes, sportsmen, stressed people, aged population, kids, pregnant women, people under malnutrition, alcoholics, patients undergoing chemo/radio therapy, asthma patients, people with poor cognition, depression, anxiety and fatigue, patients with poor electrolyte balance, sodium-potassium imbalance, anaemia patients, inflammation, gastrointestinal disorders, liver disorders, skin problems, postmenopausal women, etc.

The Neera powder can also be used to enhance the immunity, endogenous antioxidant defences, anti-inflammatory responses, anti-neuroinflammation and neuroprotective actions.

In another embodiment, animal studies have shown the beneficial pharmacological effects of the sap powder, when administered in rats/mice at 20 to 500 mg/kg body weight, anti-inflammatory markers like CRP, WBC counts, TLR-4, SGOT, SGPT, Alkaline Phosphatase (ALP), C-Reactive Protein (CRP), COX, Interleukin-6 (IL-6), Tumor Necrosis Factor-α (TNF-α), and extracellular matrix protein like Matrix metalloproteinase (MMP)-2, Matrix metalloproteinase (MMP)-9 were modulated in a health beneficial way.

In an embodiment, the mammal, subject is human being or an animal.

Hereinafter, embodiments of the present invention will be described in more detail with reference to the following examples. However, it should be understood that the following examples are provided only for illustrating the present invention and should not be construed as limiting the scope and spirit of the present invention.

Example 1

In this production 25 litres of coconut inflorescence sap is filtered through 300 mesh filter cloth. 15% w/w of gum acacia is added to the purified sap inflorescence. The mixture is homogenized using high pressure homogenizers under pressure of 30 Mpa. The homogenization process produces the uniform mixture. The homogenized mixture is subjected to spray drying to form a free flowing powder.

The spray dryer is operated in optimum temperature to provide a stable Neera powder. The spray dryer is operated at an inlet temperature of 150° C. and outlet temperature at 92° C. The overall yield is 14%.

The temperature, carrier and the homogenization will largely affect the nutrient profile of the powder Neera. The Table-1 below outlines the physicochemical characteristics and nutrient profile of Neera powder obtained by said process

TABLE 1

Physicochemical characteristics of Neera powder

| Sl. No. | Parameters | | | Results |
|---|---|---|---|---|
| 1. | Colour and appearance | | | White free flowing powder |
| 2. | Taste | | | Sweet |
| 3. | Bulk density | | | 0.2-0.5 g/mL |
| 4. | Moisture | | | 4.8% |
| 5. | Solubility | | | Soluble in water |
| 6. | Protein | | | 1.5% |
| 7. | Fat | | | 1% |
| 8. | Carbohydrate | | | 78% |
| 9. | Vitamins | | | |
| | a. | Vitamin C | | 640 ppm |
| | b. | Vitamin B | | |
| | | i | Thiamine (B1) | 2304 ppm |
| | | ii | Riboflavin (B2) | 378 ppm |
| | | iii | Niacin (B3) | 498 ppm |
| | | iv | Pyridoxine (B6) | 636 ppm |
| | | v | Biotin (B7) | 9 ppm |
| | | vi | Folic acid (B9) | 11 ppm |
| 10. | Minerals | | | |
| | a. | Potassium | | 5600 ppm |
| | b. | Magnesium | | 224 ppm |
| | c. | Phosphorous | | 218 ppm |
| | d. | Sodium | | 678 ppm |
| | e. | Zinc | | 8 ppm |
| | f. | Iron | | 42 ppm |
| | g. | Copper | | 2.1 ppm |
| | h. | Manganese | | 6.3 ppm |

Example 2

20 litres of coconut inflorescence sap is filtered through 300 mesh filter cloth. 22% w/w of Maltodextrin is added to the purified sap inflorescence. The mixture is homogenized using roto-stator homogenizer at 15,000 to 20,000 rpm to form a uniform emulsion for spray drying. The emulsion is subjected to spray drying wherein the spray dryer is operated at an inlet temperature of 130° C. and outlet temperature is 85° C. The overall yield of Neera powder is 16.2%.

The Table-2 below outlines the physicochemical characteristics and nutrient profile of Neera powder obtained by said process

TABLE 2

Physicochemical characteristics of neera powder

| Sl. No. | Parameters | | | Results |
|---|---|---|---|---|
| 1. | Colour and appearance | | | White free flowing powder |
| 2. | Taste | | | Sweet |
| 3. | Bulk density | | | 0.2-0.5 g/mL |
| 4. | Moisture | | | 4% |
| 5. | Solubility | | | Soluble in water |
| 6. | Protein | | | 1.4% |
| 7. | Fat | | | 0.8% |
| 8. | Carbohydrate | | | 76.2% |
| 9. | Vitamins | | | |
| | a. | Vitamin C | | 520 ppm |
| | b. | Vitamin B | | |
| | | i | Thiamine (B1) | 1380 ppm |
| | | ii | Riboflavin (B2) | 314 ppm |
| | | iii | Niacin (B3) | 742 ppm |
| | | iv | Pyridoxine (B6) | 921 ppm |
| | | v | Biotin (B7) | 7 ppm |
| | | vi | Folic acid (B9) | 9 ppm |
| 10. | Minerals | | | |
| | a. | Potassium | | 6200 ppm |
| | b. | Magnesium | | 178 ppm |
| | c. | Phosphorous | | 145 ppm |
| | d. | Sodium | | 900 ppm |
| | e. | Zinc | | 6 ppm |
| | f. | Iron | | 34 ppm |
| | g. | Copper | | 1.3 ppm |
| | h. | Manganese | | 5.1 ppm |

Example 3

In this production 25 litres of coconut sap juice is filtered through 300 mesh filter to remove any particulate matter. To the filtrate 18% w/w of non-digestible modified starch is added to purified coconut sap juice. Homogenization of mixture is achieved by using high pressure homogenizer and rotor-stator homogenizers. The mixture is homogenized using rotor-stator homogenizer at 15,000 rpm, followed by high pressure homogenization at pressure of 60 Mpa. The mixture is subjected to spray dryer, operated at an inlet and outlet temperature of 140° C. and 98° C. respectively. The yield of Neera powder is 15.8%

The Table-3 below outlines the physicochemical characteristics and nutrient profile of Neera powder obtained by said process

TABLE 3

Physicochemical characteristics of Neera powder

| Sl. No. | Parameters | | | Results |
|---|---|---|---|---|
| 1. | Colour and appearance | | | White free flowing powder |
| 2. | Taste | | | Sweet |
| 3. | Bulk density | | | 0.2-0.5 g/mL |
| 4. | Moisture | | | 4.3% |
| 5. | Solubility | | | Soluble in water |
| 6. | Protein | | | 1.3% |
| 7. | Fat | | | 1.1% |
| 8. | Carbohydrate | | | 76% |
| 9. | Vitamins | | | |
| | a. | Vitamin C | | 720 ppm |
| | b. | Vitamin B | | |
| | | i | Thiamine (B1) | 2100 ppm |
| | | ii | Riboflavin (B2) | 410 ppm |
| | | iii | Niacin (B3) | 712 ppm |
| | | iv | Pyridoxine (B6) | 1334 ppm |
| | | v | Biotin (B7) | 11 ppm |
| | | vi | Folic acid (B9) | 12 ppm |
| 10. | Minerals | | | |
| | a. | Potassium | | 7108 ppm |
| | b. | Magnesium | | 220 ppm |
| | c. | Phosphorous | | 212 ppm |
| | d. | Sodium | | 1378 ppm |
| | e. | Zinc | | 8 ppm |
| | f. | Iron | | 54 ppm |
| | g. | Copper | | 1.6 ppm |
| | h. | Manganese | | 5.6 ppm |

Example 4

Preparation of Coconut Inflorescence Sap Powder by Freeze-Drying

In this production 4 litres of coconut sap inflorescence is filtered through 300 mesh filter. 10% w/w maltodextrin is added to the purified sap inflorescence. The mixture is homogenized using rotor-stator homogenizer at 20,000 rpm to form a homogenized emulsion. The homogenized emulsion is subjected to freeze drying to form a free flowing powder.

The homogenized emulsion is loaded into freeze drying containers, the emulsion if frozen and −45° C. The frozen material is primary dried in vacuum at −45° C. to remove the moisture content and convert to powder. Further, the primary dried power is secondary dried to improve the product characteristics.

Dry Neera powder obtained after secondary drying has the physiochemical characteristics and nutrient profile as outlined below in Table-4

TABLE 4

Physicochemical characteristics of Neera powder

| Sl. No. | Parameters | | | Results |
|---|---|---|---|---|
| 1. | Colour and appearance | | | White free flowing powder |
| 2. | Taste | | | Sweet |
| 3. | Bulk density | | | 0.2-0.5 g/mL |
| 4. | Moisture | | | 4.8% |
| 5. | Solubility | | | Soluble in water |
| 6. | Protein | | | 1.5% |
| 7. | Fat | | | 0.9% |
| 8. | Carbohydrate | | | 77.2% |
| 9. | Vitamins | | | |
| | a. | Vitamin C | | 1490 ppm |
| | b. | Vitamin B | | |
| | | i | Thiamine (B1) | 4025 ppm |
| | | ii | Riboflavin (B2) | 725 ppm |
| | | iii | Niacin (B3) | 1029 ppm |
| | | iv | Pyridoxine (B6) | 1580 ppm |
| | | v | Biotin (B7) | 12 ppm |
| | | vi | Folic acid (B9) | 14 ppm |
| 10. | Minerals | | | |
| | a. | Potassium | | 8100 ppm |
| | b. | Magnesium | | 230 ppm |
| | c. | Phosphorous | | 242 ppm |
| | d. | Sodium | | 1515 ppm |
| | e. | Zinc | | 8 ppm |
| | f. | Iron | | 31 ppm |
| | g. | Copper | | 1.7 ppm |
| | h. | Manganese | | 5.4 ppm |

Example 5

The nephron-protective efficacy of Neera is evaluated in a mouse model administering a therapeutic effective dosage. Gentamycin, broad spectrum aminoglycoside is limited by renal impairment in most of the patients. The health benefits of coconut sap inflorescence powder/Neera powder (CSP) is evaluated in a comparative study where adult male Wistar rats into three groups. The normal control rats (Con), Gentamycin Treated (GM) (80 mg/kg) and Gentamycin with Neera powder (CSP) supplementation (GM 80 mg/kg+CSP 20 mg/kg b·wt). The Gentamycin is administered through intra-peritoneal route and Neera powder (CSP) powder is constituted with distilled water, administered orally. After the end of study at 16 days the rats were evaluated on the following parameters.

Kidney function—The gentamycin (GM) group has shown significant elevated levels of Creatinine, Uric acid and Urea levels in the serum. Supplementation of rats with Neera powder (CSP) significantly ($P<0.05$) lowered the levels of Creatinine, Uric acid and Urea. The results as shown in FIG. 1

Figure 2:
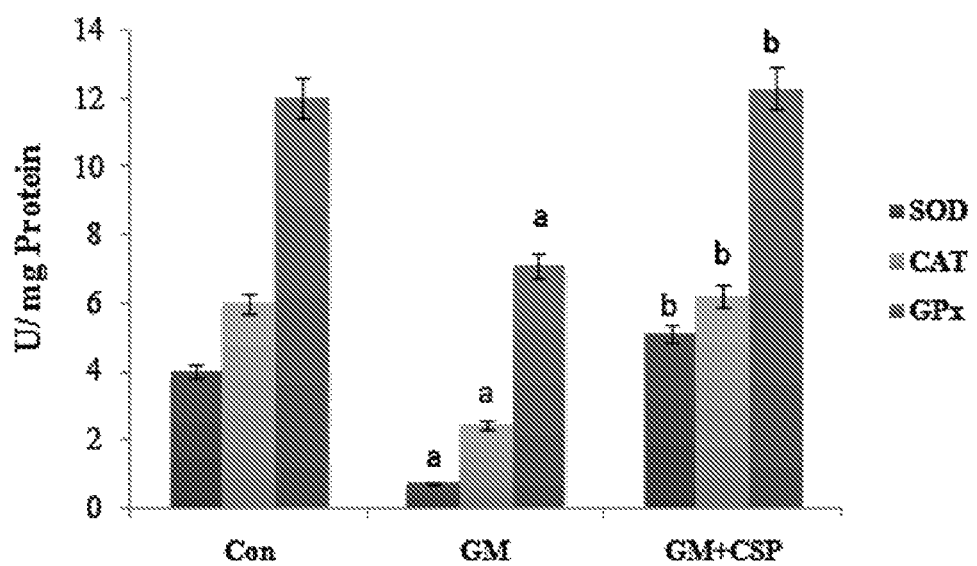
FIG. 2 shows Effect of CSP on the activities of SOD, CAT and GPx enzymes

It has also been observed that GM+CSP group has shown elevated levels of antioxidant enzymes SOD, CAT, GPx and antioxidant GSH. The results as shown in FIG. 2

Figure 3:
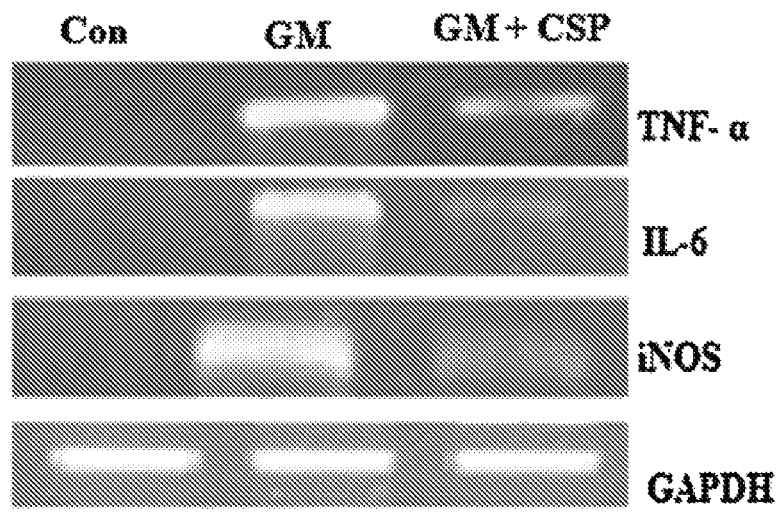
FIG. 3 shows Effect of CSP on mRNA level of TNF-a, IL-6 and iNOS

Anti-inflammatory—It is observed in the gentamycin administered group elevated levels of pro-inflammatory cytokines IL-6, TNF-α and iNOS. In the mouse group where Neera powder (CSP) is administered with Gentamycin, the up regulated levels were significantly reduced. The results as shown in FIG. 3

Figure 4:
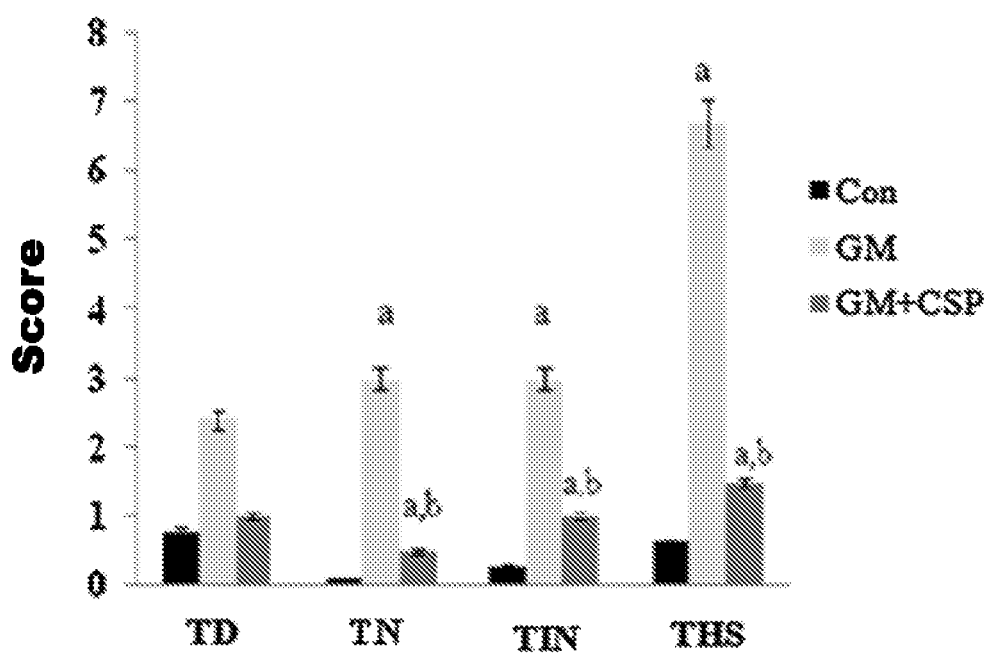
FIG. 4 shows Results of Histopathological examination performed by semi quantitatively scored from 0 to 3.

Further the histopathological assessment of kidney shows that the Gentamicin Induced (GM) rats, the kidney cells are seen in an irregular manner with massive necrosis (N), tubular degeneration (TD) and vacuolization (V). A focal interstitial nephritis made up of lymphocytes and plasma cells with desquamation of renal tubules epithelium and vacuolization are also observed. Simultaneous treatment of Gentamicin-induced nephrotoxic rats with Neera powder (CSP) shows normal arrangement of kidney cells with no evidence of necrosis. Histological scores of tubular degeneration (TD), tubular necrosis (TN), tubulointerstitial nephritis (TIN) and total histological score (THS) all increased significantly in gentamicin treated groups as compared to control group. Supplementation of Neera powder (CSP) significantly decreased the TD, TN, TIN and THS as compared to gentamicin treated group. The results as shown in FIG. 4

Example 6

The Neera powder efficacy in ameliorates alcoholic induced liver damage is evaluated in a mouse model administering a therapeutic effective dosage of Neera powder (CSP). It is evident that excessive consumption of alcohol leads to alcohol liver damage. The benefits of coconut sap inflorescence powder/Neera Powder (CSP) powder is evaluated in a comparative study where adult male Wistar rats into three groups. The normal control rats (Con), Ethanol treated rats (12.5 g/kg body weight of 90% (v/v) (ET) and Ethanol+Neera powder (CSP) treated (CSP 250 mg/kg body weight). Ethanol, CSP and distilled water (vehicle) were administrated by oral gavage (intragastrically) on every day morning after keeping them deprived of food for 10 h. After the end of study at 30 days the rats were evaluated on the following parameters.

Total WBC count was increased significantly ($p<0.05$) in ethanol treated rats as compared to the normal control group. The ET+CSP treated group, the WBC count decreased significantly ($p<0.05$) and became similar to the normal group.

Liver function—The serum SGOT, SGPT and ALP which represents the liver function are measured to estimate the liver function activity. Elevated levels are found in alcohol treated mice, whereas the Neera powder (CSP) supplemented group lowered the level of these markers to that of normal group.

Further the alcohol treated group (ET) also shown elevated levels of inflammatory markers CRP, COX, nitrite levels and molecular markers IL-6, TNF-α, TLR-4, Matrix metalloproteinase (MMP)-2, Matrix metalloproteinase (MMP)-9 whereas the CSP supplemented group were near normal and there no significant statistical difference observed between control group and CSP supplemented group.

It is also known that the ethanol decrease the activity of anti-oxidant enzymes SOD (superoxide dismutase), CAT (catalase), GSH (Glutathione) and GPx (glutathione peroxidase) which leads to sever cellular damage. Upon CSP ingestion, significant ($p<0.05$) enhancement in the levels of these antioxidant enzymes were observed indicating the survival of hepatocytes similar to the control group of rats.

The histopathology finding reveal the in the alcohol group shows probability of necrosis structures. There is no evidence of inflammation/necrosis/haemorrhage or cholestasis in CSP administered rats.

Example 7

The health benefits of Neera powder as an energy drink for athletes or personal undergoing physical exercise efficacy is evaluated in a human subject administering an effective dosage of CSP. The benefits of coconut sap inflorescence powder/Neera Powder (CSP) powder is evaluated in a comparative study where adult human subjects are divided in to control and CSP groups. The CSP is supplemented at 10 g/70 kg. body weight for 21 days for participating subjects. The blood and urine samples are analysed before and completion of the study were analysed to identify various markers.

It is evident from the results the CSP administered group had enhanced endurance levels, enhancement in performance such as speed, weight lifting ability, enhanced antioxidant enzymes (SOD, Gpx, CAT), suppression of muscle injury by diminishing the lactate levels, inhibit inflammation condition by suppressing the CRP and IL-6 levels in the blood.

We claim:

1. A process for the preparation of stable Neera powder or granulated powder, or a mixture thereof, comprising proteins, fat, carbohydrates, vitamins, minerals, and a carrier or encapsulating agent, and being suitable for oral administration, the process comprising:
   i. Obtaining a liquid unfermented coconut inflorescence sap starting material from unopened inflorescence of palm trees;
   ii. Subjecting the liquid starting material of step (i) to one filtration step to obtain a purified liquid starting material;
   iii. Mixing the purified liquid starting material of step (ii) with a carrier or encapsulating agents to obtain a mixture;
   iv. Homogenizing said mixture in step (iii) in a pressure range between 10-150 Mpa to form a homogenous mixture;
   v. Subjecting the homogenous mixture obtained in step (iv) to a spray drying process, wherein the spray drying process occurs at specified inlet temperature between 50-160° C. and outlet temperature between 85-95° C.; and
   vi. Recovering the stable Neera powder or granulated powder, or a mixture thereof,
   wherein the carbohydrate is in the range of 60 to 80%, the fat is in the range of 0.5 to 1.5%, the protein in the range of 0.5 to 2%;
   wherein the vitamins are selected from the group consisting of vitamin C, vitamin B1, vitamin B2, vitamin B3, vitamin B6, vitamin B7 and vitamin B9, and are in the range of 500-1500 ppm, 1000-5000 ppm, 200-800 ppm, 100-1000 ppm, 500-1500 ppm, 5-15 ppm and 5-15 ppm, respectively; and
   wherein the minerals are selected from the group consisting of potassium, sodium, magnesium, phosphorus, zinc, iron, copper and manganese, and are in the range of 4000-8500 ppm, 500-1500 ppm, 150-250 ppm, 145-242 ppm, 4-10 ppm, 1-3 ppm, 0.5-5 ppm, respectively.

2. The process of claim 1, wherein the carrier and/or encapsulating agent selected from the group consisting of gum acacia, gum Arabic, gum gatti, xanthum gum, maltodextrin, starch, modified starches, sugars, natural polysaccharides, dietary fibers, proteins, cereal flours, botanical extracts, polyvinyl alcohol, polyethylene glycols, and mixtures thereof.

3. The process of claim 1, wherein the Neera powder is capable of reconstitution with water, maintaining the same or enriched nutritional value of fresh coconut inflorescence sap.

4. The process of claim 1, wherein the Neera powder has a moisture content below 6%.

* * * * *